United States Patent [19]
Tal et al.

[11] Patent Number: 5,888,775
[45] Date of Patent: Mar. 30, 1999

[54] PEPTIDE SYNTHESIS AND PURIFICATION BY FUSION TO PENI PROTEIN OR PRECIPITATION EFFECTIVE PORTION THEREOF

[75] Inventors: Rony Tal, Coral Springs; Hing C. Wong, Ft. Lauderdale; Clayton Casipit, Hialeah; Pierre-Andre Chavaillaz, Cooper City; Vaughan Wittman, Ft. Lauderdale, all of Fla.

[73] Assignee: Dade International Inc, Deerfield, Ill.

[21] Appl. No.: 235,178

[22] Filed: Apr. 29, 1994

[51] Int. Cl.$^6$ .......................... A61K 39/00; C12N 15/62; C07K 1/00; C07K 19/00

[52] U.S. Cl. ...................... 435/69.7; 435/7.2; 435/252.3; 435/252.33; 435/370.7; 424/185.1; 536/23.4; 530/350

[58] Field of Search ............................. 435/69.7, 252.3, 435/252.31, 252.33, 320.1, 7.2; 424/185.1; 536/350

[56] References Cited

U.S. PATENT DOCUMENTS

| | | | |
|---|---|---|---|
| 4,952,508 | 8/1990 | Chang et al. | 435/252.3 |
| 5,215,896 | 6/1993 | Keck et al. | 435/69.7 |
| 5,258,502 | 11/1993 | Kuranda | 530/350 |

FOREIGN PATENT DOCUMENTS

| | | |
|---|---|---|
| 0244147 | 4/1987 | European Pat. Off. |
| 0 244 147 | 11/1987 | European Pat. Off. |
| 63-071178 | 3/1988 | Japan |
| 2100685 | 4/1990 | Japan |
| 92-06211 | 4/1992 | WIPO |
| 94-10308 | 5/1994 | WIPO |

OTHER PUBLICATIONS

Smith, et al., *Gene*, 67:31–40; Method and Vector Organism for Controlled Accumulation of the Cloned Heterologous Gene Production *Bacillus Subtilis* (1988).

P. Schatz, "Use of Peptide Libraries to Map the Substrate Specificity of a Peptide–Modifying Enzyme: A 13 Residue Consensus Peptide Specifies Biotinylation in *Escherichia coli*", Bio/Technology, vol. 11, pp. 1138–1143 (Oct. 1993).
D. J. Sherratt, et al., "Analysis by Transformation of the Penicillinase System in *Bacillus licheniformis*", Journal of General Microbiology, vol. 76, pp. 217–230 (1973).
D. A. Dubnau, et al., "The Genetics of *Bacillus licheniformis* Penicillinase: a Preliminary Analysis from Studies on Mutation and Inter–strain and Intra–strain Transformation", J. gen. Microbiol., vol. 41, pp. 7–21 (1965).
T. Himeno, et al., "Nucleotide Sequence of the Penicillinase Repressor Gene penI of *Bacillus licheniformis* and Regulation of penP and penI by by the Repressor", Journal of Bacteriology, vol. 168, No. 3, pp. 1128–1132 (Dec. 1986).
V. Wittman, et al., "Regulation of the Penicillinase Genes of *Bacillus licheniformis*: Interation of the pen Repressor with Its Operators", Journal of Bacteriology, vol. 170, No. 7, pp. 3206–3212 (Jul. 1988).
Imanaka, T. et al., 1981, Journal of Bacteriology, 147(3):776–788.
Imanaka, T., et al., 1992, Journal of Bacteriology, 174(4):1423–1425.
Imanaka, T., et al., 1993, Journal of Fermentation and Bioengineering 76(1):1–6.
Wong, A.C., et al., 1990, in *Genetics and Biotechnology of Bacilli*, vol. 3, Zukowski, et al., Eds., pp. 115–122.
Hiramatsu, K., et al., 1992, FEBS Letters, 298(2–3):133–136.
Wittkman, V., et al., 1993, Journal of Bacteriology, 175(22):7383–7390.

*Primary Examiner*—Charles L. Patterson, Jr.
*Assistant Examiner*—William W. Moore
*Attorney, Agent, or Firm*—Peter F. Corless

[57] ABSTRACT

The present invention provides novel methods for the synthesis and isolation and purification of a peptide of interest (target peptide). In particular, the invention relates to peptide synthesis, isolation and purification methods that comprise use of penI fusion polypeptides and related gene fusion constructs that encode such polypeptides.

38 Claims, 7 Drawing Sheets

FIG. 2

| Immunization Group | Date of Injection | Number of Mice | Dose | Route |
|---|---|---|---|---|
| F1.2 C9 KLH #3 | | | | |
| Sensitization | Day 1 | 4 | 56 ug/CFA | I.p. |
| First Boost | Day 70 | 4 | 37 ug/IFA | subcut. |
| Second Boost | Day 101 | 4 | 42 ug/IFA | subcut. |
| F1.2-C9 PEN1 #1 | | | | |
| Sensitization | Day 1 | 10 | 50 ug/CFA | I.p. |
| First Boost | Day 32 | 9 | 38 ug/IFA | subcut. |

FIG. 6

| Immunization | | Titer on F2 | Titer on F1.2-C9 KLH | Titer on F1.2-C9 Ova |
|---|---|---|---|---|
| F1.2-C9 PenI #1 | | | | |
| | Mouse #1 | 1:12,800 | 1:3200 | N.D. |
| | Mouse #2 | 1:12,800 | 1:3200 | N.D. |
| | Mouse #3 | 1:6400 | 1:1600 | N.D. |
| | Mouse #4 | 1:3200 | 1:800 | N.D. |
| | Mouse #5 | >or = 1:12,800 | >or = 1:25,600 | N.D. |
| | Mouse #6 | 1:3200 | 1:800 | N.D. |
| | Mouse #7 | 1:6400 | 1:1600 | N.D. |
| | Mouse #8 | >or = 1:12,800 | 1:12,800 | N.D. |
| | Mouse #9 | 1:6400 | 1:1600 | N.D. |
| F1.2-C9 KLH #3 | | | | |
| | Mouse #1 | 1:800 | N.D. | 1:800 |
| | Mouse #2 | 1:6400 | N.D. | 1:3200 |
| | Mouse #3 | >or = 1:12,800 | N.D. | >or = 1:25,600 |
| | Mouse #4 | 1:3200 | N.D. | 1:1600 |
| Controls | | | | |
| F1.2-C9 Ova #2 Mouse #2 | | 1:12,800 | 1:800 | N.D. |
| F1.2-C9 KLH #2 Mouse #2 | | >or = 1:12,800 | N.D. | 1:6400 |
| TA1 Monoclonal Antibody | | >or = 1:256,000 | >or = 1:256,000 | 1:32,000 |
| (Conc.= 5.7 mg/ml IgG2a) | | (22.3 ng/ml) | (22.3 ng/ml) | (178.4 ng/ml) |

FIG. 7

PEPTIDE SYNTHESIS AND PURIFICATION BY FUSION TO PENI PROTEIN OR PRECIPITATION EFFECTIVE PORTION THEREOF

BACKGROUND OF THE INVENTION

1. Field of the Invention

The present invention relates to a novel method for synthesis, isolation and purification of peptides. More particularly, the invention relates to penI fusion polypeptides, peptide synthesis, isolation and purification methods that comprise use of penI fusion polypeptides, and related gene fusion constructs that code for such penI fusion polypeptides.

2. Background

Recombinant DNA methods are employed to produce a variety of peptides. Recombinant DNA technology includes expression of a gene, either synthesized or isolated, to produce a peptide of interest. In brief, a desired DNA sequence is ligated into a cloning vector such as a plasmid. A host cell such as *E. coli*, is transformed with the cloning vector and the transformed host is then cultivated under conditions suitable for expression of the peptide coded for by the DNA sequence. The thus produced proteins are then isolated from the culture medium and typically must be purified. For example, the expressed peptide is often secreted by the host cells into the culture medium and the peptide must be separated from the culture medium and other material in that medium such as cell waste products, other peptides, etc.

Peptides also may be produced by chemical synthesis techniques, although in many applications a chemical synthetic approach may be less preferred than a recombinant procedure. For example, peptides greater than about forty or fifty amino acids in length often cannot be chemically synthesized in acceptable yields. Further, purification of relatively large chemically synthesized peptides often can be more burdensome than corresponding recombinant peptides.

A number of methods have been reported to isolate and purify proteins, including peptides produced by chemical synthesis or recombinant DNA techniques. For example, known purification methods include centrifugation, column chromatography and electrophoresis. While these methods can produce a purified peptide, they each require one or more additional and often burdensome purification steps after initial purification of the peptide. Moreover, in many current isolation and purification procedures, a significant amount of the crude peptide is lost during the procedure resulting in reduced yields.

In certain prior peptide isolation and purification schemes, hybrid or fusion polypeptides have been employed. These approaches have generally provided construction of a gene fusion that codes for a polypeptide that contains a peptide of interest linked to a peptide that exhibits specific binding characteristics not exhibited by the peptide of interest.

These prior fusion peptide methods present notable shortcomings including low yields of purified protein as well as multiple step isolation and purification protocols. For example, in EP 0244147 a fusion polypeptide is described that contains a beta-galactosidase moiety linked to a desired peptide through a renin cleavage site. To isolate and purify the desired peptide, the fusion polypeptide is adsorbed to an affinity matrix and, after eluting to remove other proteins, renin is added to the bound complex to cleave the fusion polypeptide and release the peptide of interest while the beta-galactosidase remains bound to the matrix. In a still further step the isolated peptide is purified by anion exchange chromatography.

It thus would be desirable to have new and simple methods for the synthesis and purification of peptides, particularly peptides produced by recombinant means. It would be further desirable to have such new methods that enable convenient isolation and purification of a desired peptide in a single step, particularly without significant reduction in yields.

SUMMARY OF THE INVENTION

The present invention provides a method for synthesis and purification of essentially any peptide (referred to herein as the "target peptide") by formation of a fusion polypeptide comprising the target peptide linked to the penI repressor protein, or the precipitation effective portion of the penI repressor protein.

The penI repressor protein is produced by *Bacillus licheniformis* and negatively controls the synthesis of the inducible enzyme penicillinase (penP). See Dubnau, et al., *J. Gen. Microbiol.*, 41:7–21 (1965); Sheratt, et al., *J. Gen. Microbiol.*, 76:217–230 (1973). The sequence of the penI gene, expression of that gene in *E. coli* and purification of the penI protein have been reported. See T. Himeno, et al., *J. Bacteriol.*, 68:1128–1132 (1986); Wittman, et al., *J. Bacteriol.*, 170:3206–3212 (1988).

It has been found that penI fusion polypeptides of the invention can be purified in a single step after expression of the polypeptide in a transformed host cell. Specifically, it has been found that a penI fusion polypeptide produced in accordance with the invention can be selectively precipitated from a solution by reducing the solution's ionic strength. It has thus been found that crude cell extract or supernatant thereof that contains the fusion polypeptide can be contacted with a low ionic strength aqueous solution to thereby precipitate the polypeptide. Typically a solution having a salt concentration of about 200 mM or less will be sufficient to precipitate the fusion polypeptide. A preferred means of precipitation is dialysis of a solution of the fusion peptide against a low ionic strength solution. Further purification of the precipitated material such as by reprecipitation and/or chromatography can be carried out if desired, but is not necessary for many applications.

The fusion polypeptide of the invention preferably also includes a linking sequence interposed between the penI protein and target peptide. Further preferred is where the linking peptide sequence can be recognized and cleaved by an appropriate cleavage agent, preferably without deleteriously affecting the target protein. Typically the linking sequence will include an enzyme cleavage site such as a factor Xa site.

The invention further includes DNA fusion vectors that comprise a nucleotide sequence that encodes the penI peptide, or precipitation effective portion thereof, and a sequence coding for the target peptide. Preferably the vector also includes a nucleotide sequence coding for a linking segment that is interposed between the penI protein and target peptide. The linking segment preferably can be recognized and cleaved by an appropriate cleavage agent, preferably without deleteriously affecting the target peptide.

The invention also includes fusion polypeptides that comprise the penI peptide or a precipitation effective portion thereof fused to the amino acid sequence of the target peptide. Preferably the polypeptide further includes a linking segment that is interposed between the penI protein and target peptide. As mentioned above, the linking segment preferably includes an amino acid sequence that can be recognized and cleaved by an appropriate cleavage agent without deleteriously affecting the target peptide.

The invention also includes methods using penI as an antigenic carrier. Use of a fusion polypeptide of the invention for immunization with the penI portion acting as an antigenic carrier is significantly more convenient than prior immunization methods.

The invention also includes methods for fine epitope mapping of selected peptides and preparation and use of random peptide libraries. Other aspects of the invention are discussed infra.

As used herein, the term "a precipitation effective portion of the penI protein" is defined to mean a portion of the penI protein that when fused to a target peptide will result in precipitation of the fused polypeptide upon contact (such as by method disclosed in Example 1, infra) with an aqueous solution having a low ionic strength. Thus a precipitation effective portion of the penI protein can be readily identified experimentally by those having no more than ordinary skill in the art, i.e., a gene construct can be prepared that contains a DNA sequence coding for a portion of the penI protein and a DNA sequence coding for a target peptide, that gene construct expressed, and the expressed polypeptide contacted with a low ionic strength solution as disclosed herein to determine if precipitation of the fused polypeptide occurs. Typically, at least about 50 percent of the amino acid sequence of a precipitation effective portion of the penI protein will be the same as the sequence of the penI protein, more typically at least about 70 percent of the amino acid sequence of the precipitation effective portion will be the same as the penI protein, still more typically at least about 90 percent of the amino acid sequence of that effective portion will be the same as the sequence of the penI protein. Moreover, the precipitation effective portion will typically contain at least about 50 percent of the total number of amino acid residues of pent, more typically at least about 80 percent of the total residues of penI.

BRIEF DESCRIPTION OF THE DRAWINGS

FIG. 2 illustrates the nucleic acid sequences (SEQ ID NOS: 1–10) and amino acid sequences (SEQ ID NOS: 11–20) of fusion peptides of Examples 1 and 3. In the Figure, the sequence of the F1.2-C9 target peptide of the fusion polypeptide is underlined, and the point mutations of the other penI fusion polypeptides (designated as tFPO10-tFPO18 in the figure) prepared in Example 3 are also underlined.

FIGS. 6 and 7 show the results of the immunization of with the PenI:C9 protein as detailed in Example 8.

DETAILED DESCRIPTION OF THE INVENTION

Figure 1:
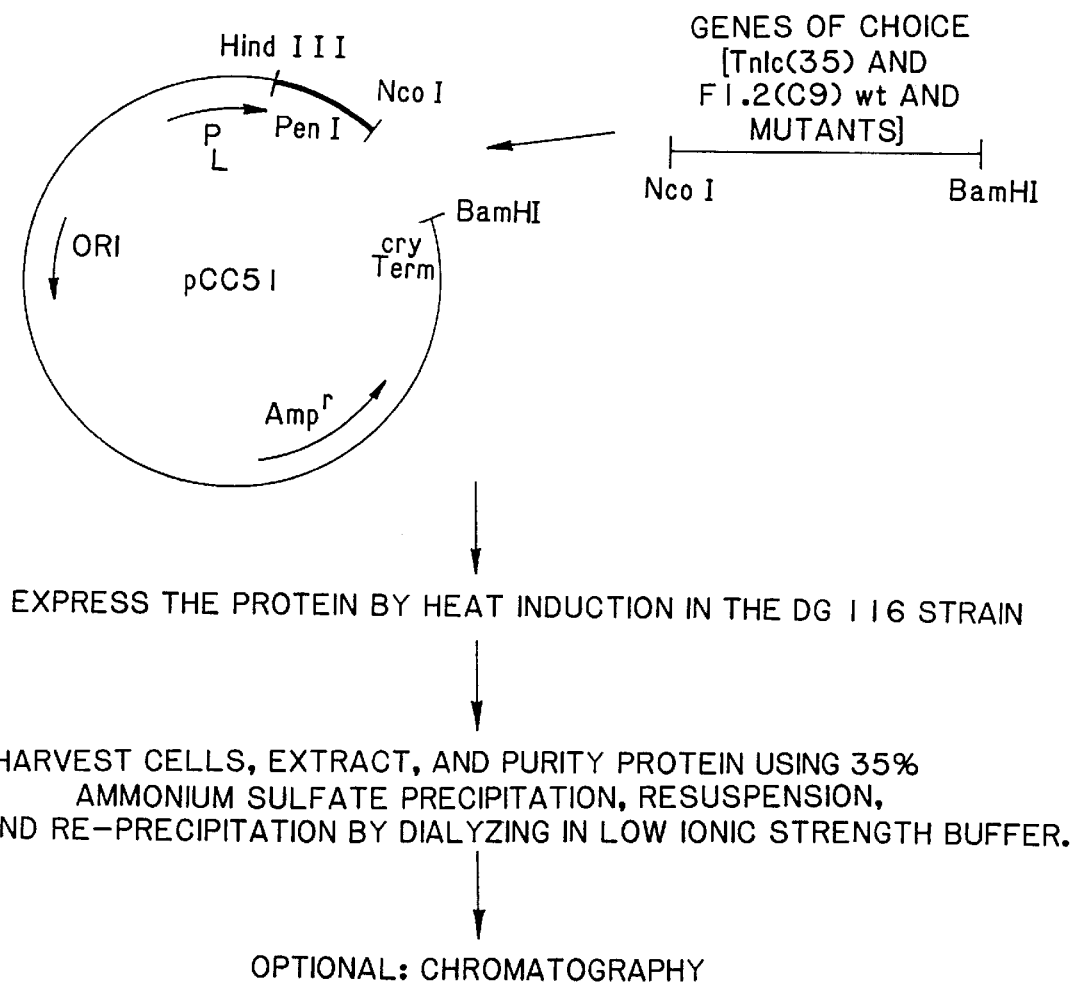
FIG. 1 illustrates the construction of the cloning vector pCC51 and use of that vector in accordance with the invention.

The present invention includes preparation of polypeptides by construction of DNA which encodes a fusion polypeptide, i.e. DNA which codes for the penI protein or precipitation effective portion thereof linked to the desired target peptide, which upon expression provides a polypeptide that comprises penI or portion thereof fused to the target peptide. The target peptide preferably is linked to the carboxyl terminus of penI protein or portion thereof, either directly or through a linking sequence. The target peptide suitably also may be linked to the amino terminus of the penI protein or portion thereof.

A fusion polypeptide also may be employed where the target peptide is flanked by portions of the penI protein whereby the flanked target peptide precipitates in a low ionic strength solution. Such a fusion polypeptide will contain two separate portions of the penI protein with the target peptide positioned therebetween. Preferably such a fusion polypeptide will contain two cleavage sites for release of the target peptide from the two "flanking" penI portions. This can be accomplished by interposing a linking segment on either side of the target peptide and between the penI protein portions, wherein those linking segments each can be recognized and cleaved by an appropriate cleavage agent.

In general, preparation of penI fusion peptides of the invention can be accomplished by recombinant DNA techniques, e.g. preparation of plasmid DNA, cleavage of DNA with restriction enzymes, ligation of DNA, transformation and culturing of host cells, etc., that are generally known to those skilled in the art and, e.g., disclosed generally in Sambrook, et al., Molecular Cloning, (2d ed. 1989).

Figure 2:
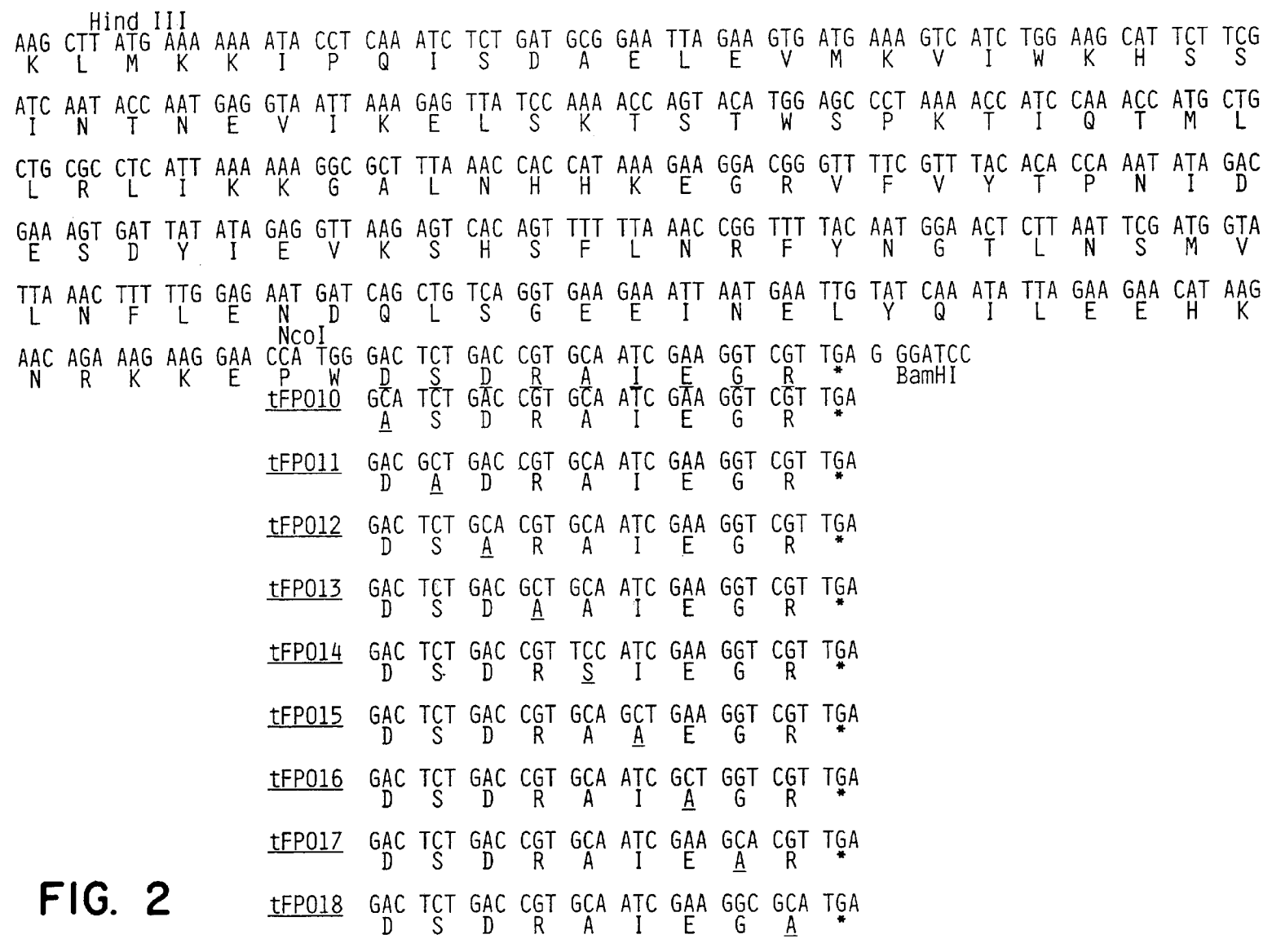

More specifically, DNA is obtained coding for the penI protein or a precipitation effective portion thereof. One source of that DNA is *Bacillus liceniformis*, which is publicly available, e.g., from the American Type Culture Collection under Accession nos. 6598, 6634 and 8480. Isolation and cloning of such DNA has been described and includes molecular cloning and polymerase chain reaction. See Wittman, et al., *J. Bacteriol.*, 170:3206–3212 (1988); and Himeno, et al., *J. Bacteriol.*, 168:1128–1132 (1986). See also Sambrook, et al., supra, including ch. 14 thereof. The nucleotide sequence coding for penI or portion thereof, or the sequence of other components of the fusion construct of the invention such as the sequence coding for the target peptide or linking segment, also can be synthesized by known methods, e.g. the phosphate triester method. See Oligonucleotide Synthesis, IRL Press (M. J. Gait, ed., 1984). Synthetic oligonucleotides also may be prepared using commercially available automated oligonucleotide synthesizers. The nucleotide and amino acid sequences of the penI protein are shown in FIG. 2 of the Drawings.

The gene coding for penI or effective portion thereof can be amplified by the polymerase chain reaction (PCR) or other means known in the art. Suitable PCR primers to amplify the penI gene may add restriction sites to the PCR product and include, e.g., an upstream primer of 5'-GGAAGCTTATGAAAAAAATACCTC-3' (SEQ ID NO: 21), and a downstream primer of 5'-GGGGATCCCTCACCATGGTTCCTTCTTTCTGTTC-3' (SEQ ID NO: 22). The penI gene can be amplified directly by standard PCR methods from *Bacillus licheniformis* chromosomal DNA using such primers or, alternatively, a suitable plasmid containing the penI gene can be used as the template for PCR. See Example 1 which follows.

To make the fusion vector, the sequence coding for penI or effective portion is linked to a sequence coding for the target protein by use of suitable ligases. DNA coding for the target peptide, optionally linked to DNA coding for a linking sequence, can be obtained by isolating the DNA from natural sources or by known synthetic methods as discussed above. A nucleotide sequence coding for penI or effective portion thereof may be directly joined to a DNA sequence coding for the target protein or, alternatively, a DNA sequence coding for a suitable linking sequence may be interposed between the sequence coding for penI and the sequence coding for the target peptide and joined using suitable ligases.

The linking sequence preferably is a nucleotide sequence that codes for a peptide that can be recognized and cleaved by a proteolytic agent that will cleave the fused polypeptide expressed by the gene construct to thereby provide the target peptide. A preferred linking sequence has a nucleotide sequence of ATCGAGGTAGG (SEQ ID NO: 23) and codes for the peptide lle-Glu-Gly-Arg, which can be cleaved by blood coagulation factor Xa. See, for example, Nagai et al., Nature, 309:810–812 (1984). A variety of other linking sequences and cleavage agents can be employed as will be recognized by those skilled in the art. Selection of a particular suitable agent will be based on the identity of the sequence of amino acid(s) at the intended cleavage site, particularly the identity of the linking sequence interposed between the penI protein or portion thereof and the target peptide. For example, suitable cleavage agents will include trypsin (cleaves at Arg, Lys), collagenase (cleaves at X-Gly-Pro), hydroxylamine (cleaves at Asn-Gly), dilute acid (cleaves at Asp-Pro), cyanogen bromide, N-bromosuccinimide, etc. Preferably the cleavage agent is selected so that it does not cleave the target protein, but reacts only with intended cleavage sites such as those positioned within the linking sequence and/or the penI protein or portion thereof. Thus, undesired cleavage can be minimized by use of cleavage agent that cleaves at a site present on the linking sequence but which is absent from the target peptide. Suitable linking sequences may be obtained by known means including oligonucleotide synthesis.

Other nucleotide sequences can be included in the gene fusion construct. For example, a promoter sequence, which controls expression of the sequence coding for the fused polypeptide, can be included in the construct or present in the expression vector into which the construct is inserted. A heat inducible promoter is particularly suitable. Similarly a signal sequence can be included in the gene construct, if desired, so that the expressed polypeptide can be secreted from the transformed host cells into the culture medium.

A number of strategies can be employed to express the fused polypeptide. For example, the gene fusion construct as described above can be incorporated into a suitable vector by known methods such as by use of restriction enzymes to make cuts in the vector for insertion of the construct followed by ligation. The vector containing the gene construct is then introduced into host cells for expression of the gene fusion. See, generally, Sambrook, et al., supra. Selection of suitable vectors can be made empirically based on factors related to the cloning protocol. For example, the vector should be compatible with, and have the proper replicon for the host cell that is being employed. Further the vector must be able to accommodate the DNA sequence coding for penI protein or portion thereof and the target peptide. Suitable host cells will include essentially any eukaryotic or prokaryotic cell, preferably those cells that can be easily transformed and exhibit rapid growth in culture medium. Specifically preferred host cells include prokaryotes such as E. coli, Bacillus subtilis, etc. and eukaryotes such as animal cells and yeast strains, e.g., a strain of the genus Saccharomyces such as S. Cerervisiae. Other suitable hosts include, e.g., insect cells such as Sf9. The transformed host cells are typically multiplied in a selective growth medium, e.g. an antibiotic (assuming the cloning vector includes an appropriate resistance gene). The host cell containing the fusion vector is cultured and the fused gene is induced, if necessary, by conventional techniques.

In one suitable protocol the PCR product of the penI gene is cloned into a suitable vector such as the E.coli vector pUC19. Other vectors that may be suitably employed are known in the art, may be selected as disclosed above and include, e.g., pBR322. The isolated DNA coding for the target peptide is then cloned into the vector containing the penI gene. See, for example, FIG. 1 of the Drawings. The construct is then used to transform an appropriate host such as E. coli by known methods. See Sambrook, et al., supra. As mentioned above, transformants are selected by conventional means e.g. by including an appropriate marker gene into the construct which imparts a detectable phenotypic property to transformed cells. For example, transformants can be identified by antibiotic (e.g. tetracycline) selection where the transformants contain the appropriate resistance gene. The host cell containing the fusion vector is cultured and the fused gene is induced, if necessary, by conventional techniques. For example, for at least certain systems, the cell culture can be suitably incubated by heating with agitation. The cells are then harvested and, if necessary or desired, lysed. The culture medium can be optionally centrifuged to remove various cell debris and other materials, and then is contacted with an aqueous solution having an ionic strength sufficient to precipitate the fused polypeptide. In one particularly preferred aspect of the invention, the fused polypeptide is precipitated from the culture medium or other solution by dialysis against a low ionic strength buffer, e.g., a solution having a salt concentration of about 250 or 200 mM or less, more preferably about 100 mM or less. A 50 mM KCl buffer solution is particularly preferred.

In general, the fused polypeptide will precipitate from a solution having a salt concentration of about 200 mM or less, typically from a salt concentration of about 200 mM to 50 mM. A dialysis procedure as described in Example 1 and elsewhere herein is a particularly preferred method for precipitating the fused polypeptide, although other methods for precipitating the polypeptide by contact with a low ionic strength buffer can be employed. For example, the penI fusion polypeptide in solution simply can be admixed with such a low ionic strength solution.

The conditions under which the polypeptide solution is contacted with the low ionic strength solution, e.g., rate of addition of buffer solution, temperature of buffer solution and polypeptide solution, etc., can be optimized with no more than routine experimentation to selectively precipitate the desired fusion polypeptide from other materials that may be present in the solution. For example, the fusion polypeptide solution can be contacted with the low ionic strength solution under selected conditions; yields and purity of the precipitated polypeptide obtained under the varying conditions will indicate the optimal parameters for precipitation of that polypeptide.

Similarly, suitable aqueous solutions having an ionic strength sufficient to precipitate the penI fusion polypeptide can be readily identified. For example, samples of a fusion polypeptide of the invention in solution can be treated with aqueous solutions having differing ionic strengths to thereby determine the optimum solution for precipitation of that fusion polypeptide.

The solution used to precipitate the fusion polypeptide preferably contains at least one salt. A number of salts known in the art may be employed including alkali metal or alkaline earth metal salts such as a sodium halide salt e.g. NaCl. It is generally preferred to employ a potassium salt, particularly a potassium halide such as KCl. The aqueous solution also typically contains a buffer such as Tris or other known agent to maintain pH at a desired level. The solution also may include other optional components, e.g., a protease inhibitor such as phenylmethylsulfonyl fluoride (PMSF).

It has been found that the initial concentration of the penI fusion polypeptide in solution prior to precipitation can affect recovery and purity of the precipitated polypeptide. Specifically, it is typically preferred that the fusion polypeptide be present in solution at a concentration of about 0.3 to 1.0 mg per millimeter of solution, although concentrations outside this preferred range also will be suitable, particularly higher concentrations. Such preferred concentrations of the fused polypeptide in a culture medium can be readily achieved in most cases, particularly when using the vector and heat induction system as described in Example 1 which follows. That vector and induction system typically results in expression wherein the penI-target peptide fusion constitutes about $\geq 20$ wt. % of total cell protein.

It has been found that fusion polypeptides of the invention can be isolated in high purity from solution. For example, recombinant penI fusion polypeptides of the invention have been isolated from *E. coli* cells at a purity (HPLC analysis) of 50 percent or greater, and even at a purity of about 85 percent or greater.

It also has been found that penI fusion polypeptides of the invention can be isolated in high yields from a culture medium, e.g., at about 15 percent or greater of the total expressed polypeptide, and even yields of about 25 percent or greater. More specifically, the yield is often about 3 and 9 mg of polypeptide per $10^{11}$ *E. coli* cells. As will be appreciated by those skilled in this art, such yields are significantly higher than yields provided by prior isolation and purification methods.

The precipitated polypeptide may be employed without further purification or, optionally, it may be subjected to further purification steps. For example, the polypeptide can be dissolved in a suitable solution of relatively high ionic strength and then precipitated by contact with a low ionic strength buffer, particularly by dialysis against a low ionic strength buffer solution. The precipitated polypeptide also can be further purified by conventional techniques such as chromatography.

The purified polypeptide may be suitably used in its fused form, particularly where the biological properties of the target peptide are not deleteriously inhibited by the penI protein or portion thereof, or by the linking sequence (if present).

Alternatively, the target peptide can be released from the penI protein or portion thereof by treating the fused polypeptide with a suitable cleavage agent. In particular, if the polypeptide includes a linking segment as discussed above, the polypeptide can be treated with an appropriate cleavage agent to thereby cleave the polypeptide.

Virtually any peptide or protein can be purified in accordance with the present invention as long as the target peptide does not prevent precipitation of the fusion polypeptide of the invention (i.e., the peptide comprising the penI protein and the target peptide) in a low ionic strength buffer as specified above. Suitable target peptides can be readily identified by those skilled in the art, e.g., by sequential steps of 1) expressing a fusion vector as described above to provide a polypeptide that comprises penI or precipitation effective portion thereof and the target peptide of interest, 2) contacting that polypeptide in solution with a suitable low ionic strength buffer, and 3) observing the solution for precipitation of the polypeptide.

Certain characteristics of the target peptide either individually or in combination potentially can prevent or at least inhibit precipitation of a fusion polypeptide of the present invention. Specifically, the size of the target peptide and the number of charged moieties present on that peptide can affect precipitation of the fusion polypeptide. Thus, generally the target peptide comprises about 200 or less amino acids, more preferably about 140 or less amino acids, still more preferably comprising about 120 or less amino acids, even more preferably about 100 or less amino acids, most preferably about 70 to 80 amino acids or less. Larger target peptide portions could interfere with the ability of a fusion polypeptide to precipitate from solution. It is also preferred that the target peptide does not contain an excessive number of charged groups, i.e., either charged acidic or basic groups, which also could interfere with the ability of the polypeptide to precipitate from solutions of low ionic strength. Accordingly, preferably no more than about 10 to 20 percent of the total number of amino acids of the target protein are acidic or basic amino acids such as Lys, Arg, His, Asp or Glu.

Specific examples of peptides that can be synthesized and purified in accordance with the invention include, e.g., enzymes, transferases, lyases, isomerases, antigens or antigenic determinants, immunogens, proteins that form structural elements of animals, DNA binding peptides, peptides involved in protein/protein interaction, etc. Further, the invention is not limited to naturally occurring proteins, but also includes preparation and purification of synthetic peptides, i.e. peptides that do not occur in nature, including analogs of the above-mentioned proteins wherein one or more amino acids is different than the naturally occurring peptides, fragments of the above-mentioned naturally occurring peptides, and other synthetic peptides.

Polypeptides produced in accordance with the invention will have a wide variety of uses. For example, the fusion polypeptide can be used for immunization with penI or portion thereof acting as an antigenic carrier molecule for the target peptide. See, for instance, Example 8 which follows. Such a procedure is significantly more convenient than prior methods for use of non-immunogenic antigen. Those prior methods provide for chemical linkage of the previously prepared or isolated antigen to a carrier such as BSA or KLH followed by one or more purification steps. In contrast, by using penI as the carrier, an effective antigen can be prepared and isolated in high purity in a single step. These antigens can be used to produce polyclonal and monoclonal antibodies, specifically by administering a fusion polypeptide of the invention to a mammal such a mouse or rabbit, wherein that administration elicits a desired immune response, i.e., production of antibodies specific for epitope (s) of the polypeptide. The harvested antibodies can be used for a variety of applications as will be recognized by those skilled in the art including in various assays and diagnostics.

The invention also includes epitope mapping or epitope identification of a target peptide. In general, a peptide is prepared by the methods of the invention and the binding activity of that peptide with respect to a binding domain of a peptide or polypeptide (e.g., an antibody) is determined. The binding activity of a fusion peptide of the invention may be determined or, alternatively, the fusion peptide may be cleaved with an appropriate cleavage agent, the target peptide isolated, and the binding activity of the target peptide evaluated. More particularly, a group of penI fusion polypeptides having related sequences, e.g. each differing by only about 1–5 or 1–3 amino acids, can be isolated by contact with a low ionic strength buffer. To identify epitope (s) of the peptides, the binding activity of the isolated peptides to the binding domain of a particular peptide or polypeptide such as a monoclonal or polyclonal antibody can be determined through use of, e.g., a biosensor system using surface plasmon resonance detection, western blot analysis, or ELISA. See, for instance, Examples 3 and 4 which follow.

The invention also includes preparation and use of a random peptide library. For example, DNA sequences encoding a variety of peptides can be cloned into an expression vector system such as those identified above that contains a DNA sequence encoding the penI protein or precipitation effective portion thereof and, optionally, a linking sequence coding for a peptide sequence that contains one or more cleavage sites. Preferably restriction fragments of an appropriate cDNA library or genomic DNA library (see Sambrook, et al., supra) are used as the source of sequences inserted into the expression vector. Suitably those sequences are inserted in the expression vector downstream of the gene coding for penI or portion thereof and linking sequence, if present. Suitable host cells, e.g. those identified above such as E. coli cells, are transformed with the vector containing the gene fusion (i.e., the sequence coding for penI or portion thereof and the additional peptide). Transformants are cultured under suitable conditions, e.g. grown on a solid substrate such as a nylon membrane. The resulting cells are then screened for expression of fusion polypeptide(s) of interest by standard techniques such as by use of labelled antibody. See Methods in Enzymology, volume 152, Guide to Molecular Cloning Techniques, (S. Berger et al., ed., 1987). Polypeptides expressed from the selected clones then can be readily isolated and purified by contact with a low ionic strength solution to precipitate the polypeptide as disclosed above. The peptide of interest can be cleaved from the penI segment of the polypeptide if the polypeptide includes a suitable cleavage site such as a factor Xa site within a linking segment.

All documents mentioned herein are incorporated by reference herein in their entirety.

The following non-limiting examples are illustrative of the invention.

EXAMPLE 1

To construct a suitable expression vector containing the penI gene, the penI gene was amplified by the Polymerase Chain Reaction (PCR) using standard techniques from the plasmid pCC34 as template. The plasmid pCC34 was a PUC19 vector containing the penI. Conditions of the PCR were as follows: 100 ng of the plasmid pCC34 was used as template, 10 pmoles of the primers FX-1 and FX-2 (identified immediately below), 50 mM KCl, 20 mM Tris-HCl pH 8.4, 2 mM $MgCl_2$, 100 µg/ml Bovine Serum Albumin, 50 µM dNTP, 2.5 units of Taq DNA polymerase (Cetus Perkin-Elmer) in a 100 pil final volume. The reaction was run for 25 cycles at 95° C., 55° C. and 72° C. The penI gene also could be amplified by standard PCR techniques directly from Bacillus liceniformis chromosomal DNA using these same primers. The above-mentioned PCR primers used to amplify the penI gene were:
Upstream primer (FX-1)
    5'-GGAAGCTTATGAAAAAAATACCTC-3' (SEQ ID NO: 24)

Downstream primer (FX-2)
    5'-GGGGATCCCTCACCATGGTTCCTTCTTTCTG-TTC-3' (SEQ ID NO: 25)

The upstream PCR primer was designed to add a HindIII restriction site at the 5' end of the PCR product and the downstream PCR primer was designed to add NcoI and BamHI restriction sites at the 3' end of the PCR product. The PCR product was digested with HindIII and BamHI and cloned into the HindIII-BamHI sites of the E. coli vector pUC19. As a result, this vector (tET002-3) contains the penI gene construct flanked by HindIII at the 5' end and NcoI and KpnI at the 3' end. The sequence of the cloned penI gene was confirmed using the ABI DNA sequencing apparatus and the M13 (+/−) universal sequencing primers.

To demonstrate that a fusion peptide could be expressed at high levels in E. coli the following oligonucleotides were designed and synthesized by the ABI oligonucleotide synthesizer:
Upstream primer (ET003)
    5'-CATGGGACTCTGACCGTGCAATCGAAGGTCG-TTGAGGGATCCGGTAC-3' (SEQ ID NO: 26)
Dowstream
    5'-CGGATCCCTCAACGACCTTCGATTGCACGGT-CAGAGTCC-3' (SEQ ID NO: 27)

These oligonucleotide were annealed to each other as described below and cloned into the NcoI-KpnI site of the plasmid tET002-3. 100 pmoles of each oligonucleotide were boiled for 10 minutes in the presence of 44 mM EDTA and 66 mM NaCl and cooled slowly to room temperature. These annealed oligos where cloned into the NcoI-KpnI sites at the 3' end of the penI gene. This plasmid was designated pCC50. The gene construct, from the HindII site 5' of the penI gene to the BamHI site 5' of the KpnI site, was then subcloned into the expression vector pDG160, via the HindIII/BamHI sites, oriented 3' to the PL promoter. When properly expressed, this gene will encode the penI protein fused in frame to the following 9 amino acid peptide: Asp Ser Asp Arg Ala lieu Glu Gly Arg. The first two amino acid residues are P Y which are encoded by the NcoI codons and the following 9 amino acid residues designated C9 herein, are identical to the carboxy terminus of the factor Xa cleaved blood factor pro thrombin. This plasmid was designed pCC51, and the oligonucleotide sequence between the NcoI and the SalI sites has also been confirmed as described above.

EXAMPLE 2

To express a large amount of the fusion peptide penI:C9, a 500 ml culture of strain DG116:pCC51 was grown in M9 medium (Per 1 liter volume, add 6 g of $Na_2HPO_4$ sodium phosphate dibasic, 3 g $KH_2PO_4$, 0.5 g NaCl and 1 g $NH_4Cl$ and autoclave. Make the following sterile additions: 10 ml of 20% glucose, 10 ml of 0.01M $CaCl_2$, 1 ml of 1M $MgSO_4$: $7H_2O$, 20 mg B1 (final concentration of 20 µg/ml), 5 g Casamino acids (Norit treated, final concentration 0.5%) and 50 µg/ml ampicillin) at 30° C. to an OD of 0.5–0.8. The culture was subjected to a heat shock to induce expression from the PL promoter of the plasmid by incubating it for 5–15 minutes at 42° C. The culture was then incubated with shaking at 39° C. for additional 1–2 hr. The cells were harvested and resuspended in 10 ml of Lysis Buffer (LB) (per 200 ml volume add: 20 ml of 1M Tris buffer [pH 8.0], 20 ml of 2M KCl, 0.8 ml of 0.25 EDTA, 04 ml of 1M $CaCl_2$, 1 ml of 2M $MgCl_2$, 20 µl of 0.1M DTT, 12.5 ml of 80% glycerol and 145.28 ml of H20). The cells were then disrupted in a french press at a pressure of 1500 PSI. The french press was washed with 10 ml of SB buffer (per 500 ml add: 50 ml of 1M Tris [pH 8.0], 10 ml of 1M CaCl$_2$, 0.5 ml of 1M DTT, 259 ml of 80% Glycerol and 189.5 mls of H$_2$O)+200 mM KCl. The final volume was recorded at 17 ml. A 10% solution of polyethyleneimine was slowly added to a final concentration of 0.6%. The sample was centrifuged at 4° C. at 6000 RPM in a Beckman J2-HS rotor JA-20. The supernatant was removed and saved. To extract pellet (DNA) associated protein, the pellet was resuspended in 5 ml of SB buffer+600 mM KCl and was shaken at 4° C. for 1 hr. The sample was then centrifuged and the supernatant was added to the saved one. The combined supernatant was stirred in an ice bath and ammonium sulfate was slowly added to a final concentration of 35% w/v. The sample was centrifuged at 4° C. at 6000 RPM for 1 hr and the pellet kept. The pellet was redissolved in 10 ml of SB buffer+50 mM KCl, loaded into a dialysis bag and dialyzed with 2 changes of 400 mls of buffer overnight at 4° C. overnight. The precipitated material is collected by gentle centrifugation, washed with SB+50 mM KCl. The pellet is redissolved in 300 μl of 2M KCl, and add 100 μl of 10×SB buffer and slowly add 600 μl of H$_2$O (final buffer concentration was SB+600 mM KCl). To evaluate the purity of the penI:C9 a 20 μl sample is resolved on a 12.5–15% SDS-PAGE.

EXAMPLE 3

To examine the effect of each of the nine amino acid residues in the peptide C9, each was separately substituted with alanine, except the alanine in position 5 which was substituted with serine. See FIG. 2 where the DNA and amino acid sequences of each of the muteins (labeled tFPO1 0-tFPO18) are identified. To construct the vectors expressing these PenI:C9 muteins, the following complementary oligonucleotide pairs containing the codon for alanine in each position of the C9 peptide were designed:

KM1-1 upstream
  CATGGGCATCTGACCGTGCAATCGAAG-GTCGTTGAGG (SEQ ID NO: 28)
KM1-2 downstream
  GATCCCTCAACGACCTTCGATTGCACG-GTCAGATGCC (SEQ ID NO: 29)
KM2-1 upstream
  CATGGGACGCTGACCGTGCAATCGAAG-GTCGTTGAGG (SEQ ID NO: 30)
KM2-2 downstream
  GATCCCTCAACGACCTTCGATTGCACG-GTCAGCGTCC (SEQ ID NO: 31)
KM3-1 upstream
  CATGGGACTCTGCACGTGCAATCGAAG-GTCGTTGAGG (SEQ ID NO: 32)
KM3-2 downstream
  GATCCCTCAACGACCTTCGATTGCACGT-GCAGAGTCC (SEQ ID NO: 33)
KM4-1 upstream
  CATGGGACTCTGACGCTGCAATCGAAG-GTCGTTGAGG (SEQ ID NO: 34)
KM4-2 downstream
  GATCCCTCAACGACCTTCGATTG-CAGCGTCAGAGTCC (SEQ ID NO: 35)
KM5-1 upstream
  CATGGGACTCTGACCGTTCCATCGAAG-GTCGTTGAGG (SEQ ID NO: 36)
KM5-2 downstream
  GATCCCTCAACGACCTTCGATGGAACG-GTCAGAGTCC (SEQ ID NO: 37)
KM6-1 upstream
  CATGGGACTCTGACCGTGCAGCTGAAG-GTCGTTGAGG (SEQ ID NO: 38)
KM6-2 downstream
  GATCCCTCAACGACCTTCAGCTGCACG-GTCAGAGTCC (SEQ ID NO: 39)
KM7-1 upstream
  CATGGGACTCTGACCGTGCAATCGCTG-GTCGTTGAGG (SEQ ID NO: 40)
KM7-2 downstream
  GATCCCTCAACGACCAGCGATTGCACG-GTCAGAGTCC (SEQ ID NO: 41)
KM8-1 upstream
  CATGGGACTCTGACCGTGCAATCGAAG-CACGTTGAGG (SEQ ID NO: 42)
KM8-2 downstream
  GATCCCTCAACGTGCTTCGATTGCACG-GTCAGAGTCC (SEQ ID NO: 43)
KM9-1 upstream
  CATGGGACTCTGACCGTGCAATCGAAG-GCGCATGAGG (SEQ ID NO: 44)
KM9-2 downstream
  GATCCCTCATGCGCCTTCGATTGCACG-GTCAGAGTCC (SEQ ID NO: 45)

The oligonucleotide pairs were annealed to each other as described before, cloned into the NcoI-BamHI site of the vector pCC50 and the DNA sequence was confirmed as described before, and the entire PenI:C9 constructs were subcloned into the pDG160 expression vector as described before. Each of these plasmids was introduced into the *E. coli* strain DG116 as described before, and the cognate penI:C9 peptides expressed and purified as described above. The binding of the purified PenI:C9 muteins to the TA1 antibody (TA1) was examined by several methods: 1. Western-Blot analysis. 2. ELISA, and 3. BlACore Analysis.

EXAMPLE 4

In order to analyze the different binding of the different PenI:C9 muteins to the TA1 antibody (TA1 was raised from a mouse that had been immunized with F1.2-C9 KLH by standard procedures; F1.2-C9 is the purified factor Xa cleavage product of prothrombin), a biosensor system using surface plasmon resonance detection (BlAcore, Pharmacia-Biosensor) has been used. This system records the binding of the antigen to the immobilized TA1 in real time.

TA1 has been chemically immobilized onto the carboxymethylated dextran matrix of the sensor chip (CM5) using the amine coupling kit and the method provided by the manufacturer (Pharmacia Biosensor). For this purpose TA1 was diluted to 57 μg/mL in 10 mM Na-acetate buffer pH 4. After activation of the sensor chip with 30 μl of a 1:1 mixture of 11.5 mg/mL N-hydroxysuccinimide (NHS) and 75 mg/ml N-ethyl-N'-(dimethylaminopropyl) carbodiimide (EDC) 5 μL of the TA1 solution was injected at a flow rate of 3 μL/min. Residual dextran binding sites were inactivated by treatment of the chip surface with 37 μL of 1M ethanolamine pH 8.5. This resulted in the immobilization of 4541 resonance units (RU) of TA1.

The mono-S chromatography purified PenI:C9 muteins, PenI:C9 wild type (identified in Examples 1 and 3 above and FIG. 2) and the native PenI alone were diluted to 30 μg/mL in eluent buffer containing P20 (10 mM HEPES, 150 mM NaCl, 3.4mM EDTA, 0.005% P20 surfactant, pH 7.4) of the biosensor system. The BlACore program was set up as follows: Flow rate: 5 μl/min. Injection of 25 μL of PenI-peptide. Injection of 5 μL of 25 mM NaOH which regenerates TA1 by stripping of the PenI:C9 peptide. Report points were set 1. at 10 sec before the sample injection (baseline), 2. at 10 sec before the NaOH injection and 3. at 100 sec after the NaOH injection (regeneration).

Figure 3:
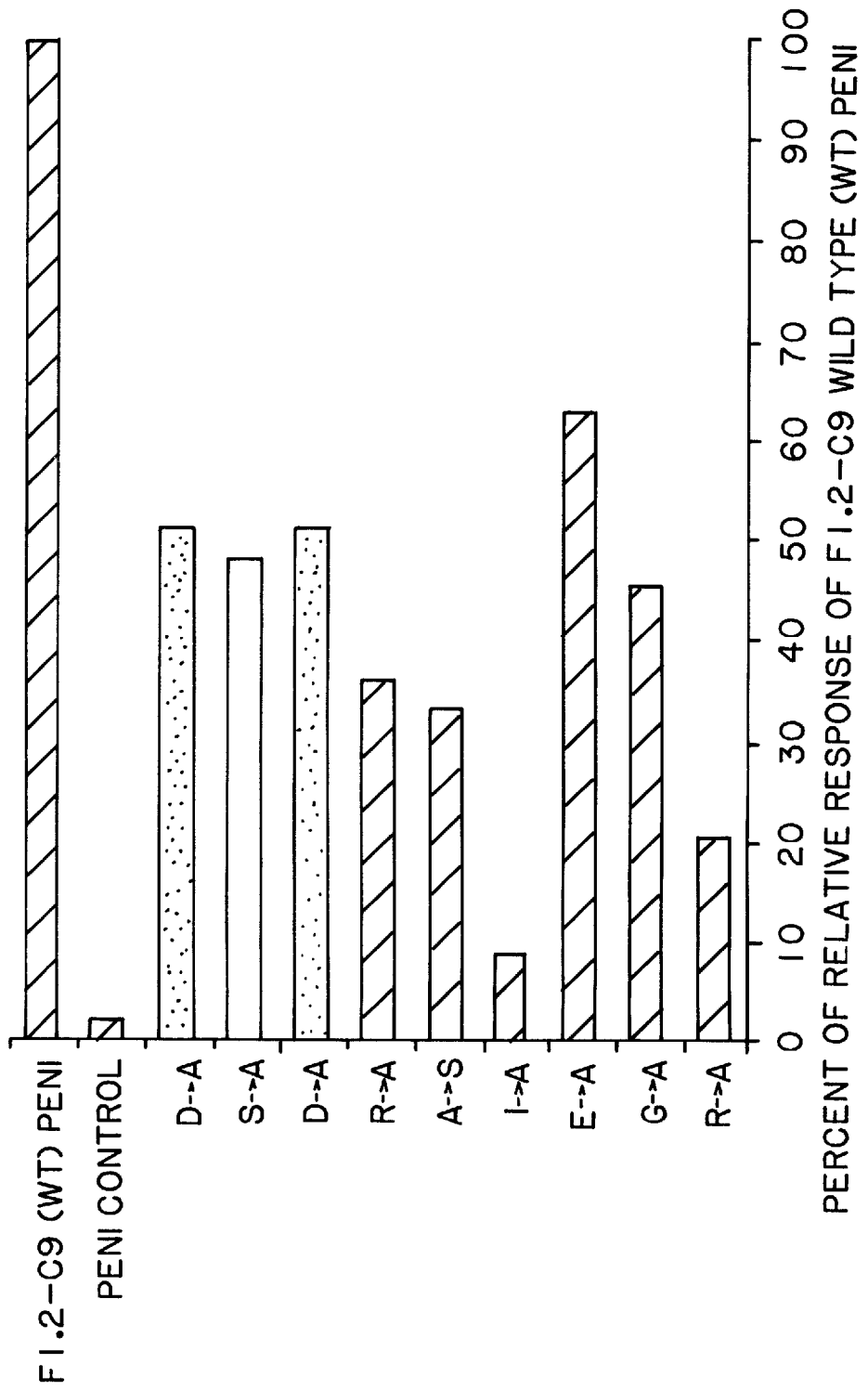
FIG. 3 shows the results of the real time Biospecific Interaction Analysis (BlAcore analysis) of Example 4.
Figure 4:
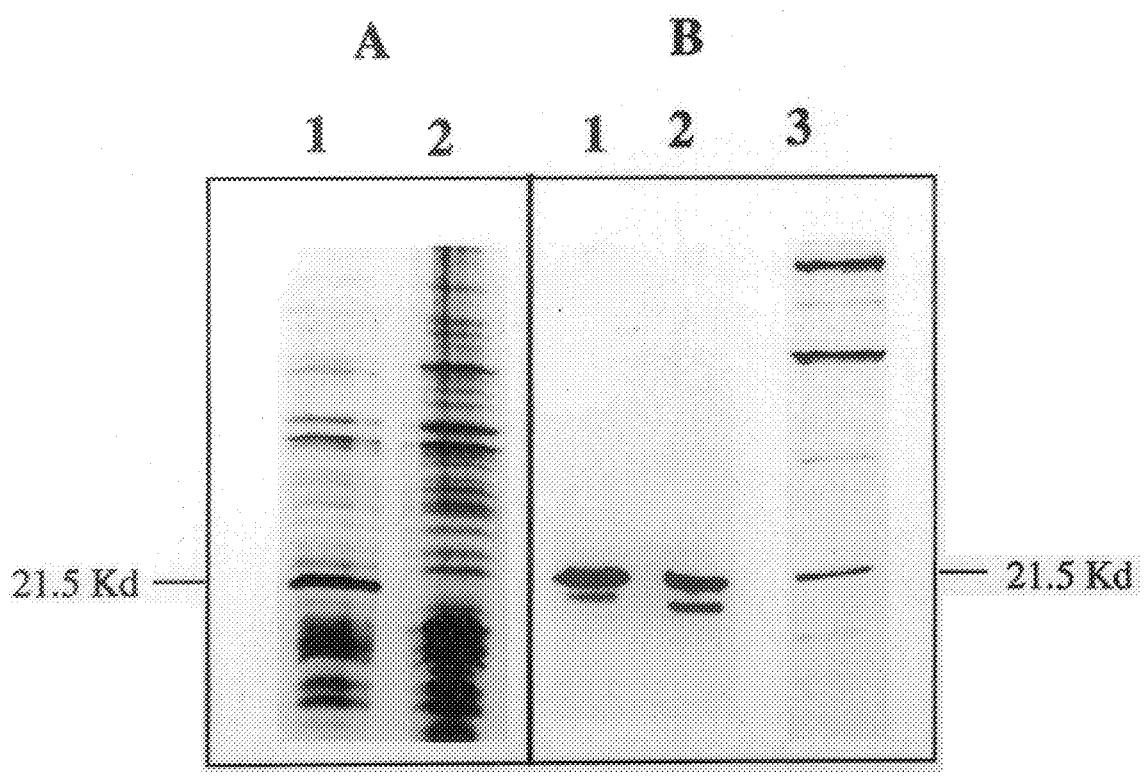
FIG. 4 shows the Western Blot and SDS polyacrylamide gel electrophoresis gel of PenI:Troponin fusion protein produced and purified in accordance with the invention. In that Figure, lane A-1 is the SDS PAGE of induced/total protein; lane A-2 is the SDS PAGE of uninduced/total protein; lane B-1 shows post cell breakage/western blot/total protein; lane B-2 shows purified (35% ammonium sulfate cut)/western blot; and lane B-3 shows purified (35% ammonium sulfate cut)/SDS PAGE.
Figure 5:
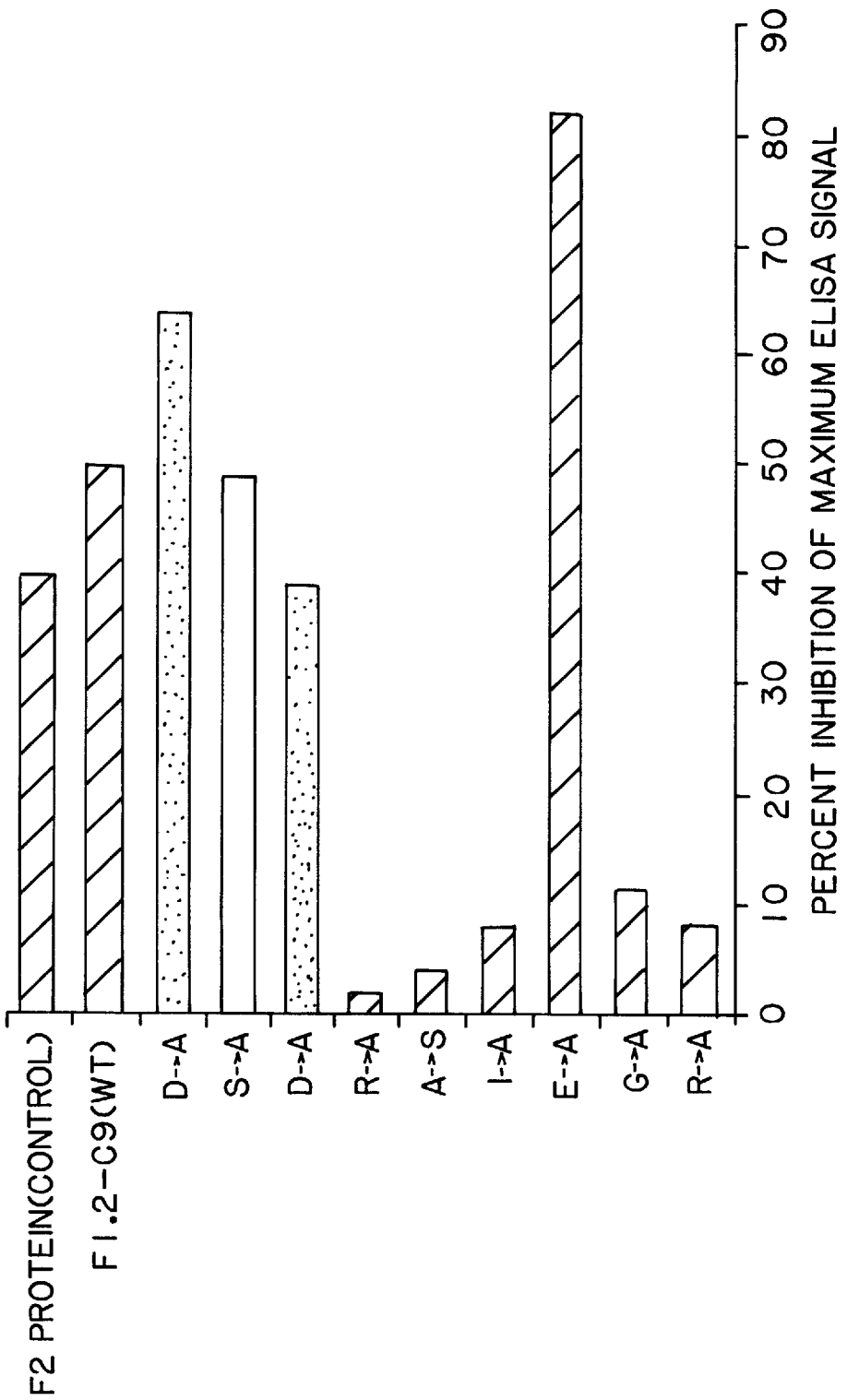
FIG. 5 shows the results of the competitive ELISA assay of fusion peptide of Example 6.

Each PenI:C9 and the native PenI protein was injected according to this program and a relative response in RU which represent the amount of penI:C9 mutein bound, was calculated by subtracting the RU of report point 1. from report point 2. Percent of binding was then calculated by setting the relative response of the wild type to 100%. Native PenI containing no C9 fusion peptide, didn't show a significant binding (<5%) to TA1. The seven PenI:C9 muteins showed 65–35% less binding to Ta1 as compared to the wild type PenI:C9. The binding results are detailed in FIG. 3 of the Drawings. The most dramatic reduction of binding was noticed when the isoleucine in the C9 peptide has been substituted with alanine; in this case the binding was only 10% compared to the wild type PenI:C9. The substitution of the carboxy terminal arginine to alanine also resulted in a significant reduction of binding to TA1 to only 20% compared to the wild type.

EXAMPLE 5

Expression of a PenI:TroponinI and PenI:SH2 Fusions

Additional penI fusion polypeptides were expressed and isolated, the first including a target peptide containing the 35 amino acid TroponinI epitope (amino acids 26–60, TnI 35, of the mature human TroponinI, which is recognized by the monoclonal antibodies (mAB's) 2F6.6 and 2B1.9), and the second fusion containing a target peptide portion of the SH2 domain of GAP-N.

The DNA fragment encoding TnI35 was amplified by standard PCR techniques from a plasmid containing the TnI gene with the following primers:

Forward primer RTB#29:

GGGGCCATGGATCGAAGGTCGTAC-TAGTCGCGCTTATGCCACG (SEQ ID NO: 46) and the backward primer RTB#30:

CCCCGGATCCTCACAGCTCTTGCTTTGCAATCGT (SEQ ID NO: 47).

The PCR product was digested with NcoI and BamHI and cloned into the vector pCC51 as described in Example 1 above. The resulting plasmid pCC51:PenI-TnI 35 was introduced into the *E. coli* strain DG116 and the resulting strain was induced for expression of the fusion protein as described in Example 1 above. The soluble fraction of these cells was processed as described before and the purified fusion peptide was analyzed by SDS-PAGE and Western-Blot analysis. See FIG. 4. The results indicated that this fusion peptide is expressed up to 20% of total cell protein. The fusion peptide was purified as described in Example 1 above except that 10 mM PMSF was added to the buffers used throughout the purification process. Approximately 40% of the recovered peptide has been processed from its carboxy terminus during the purification process, suggesting that this fusion peptide may be labile under these conditions although it is stable intracellularly.

Similarly, the SH2 domain of GAP-N (92 amino acids in length) was fused to the PenI gene. The DNA fragment encoding the SH2 domain was cloned as follows. An overlap PCR was done using the primers:

CLC 107 upstream

GAGAGAAAGCTTATGAAAAAAATACCTCAAAT (SEQ ID NO: 48)

CLC 108 downstream

GGAGCCGCCACCACCGCTGCCACCAC-CGCCAGAACCGCCGCCACCTTC CTT CTTTCT-GTTCTTAT (SEQ ID NO: 49)

CLC 109 upstream

GGTGGCGGCGGTTCTGGCGGTGGTG-GCAGCGGTGGTGGCGGCTCCTGGTG GTAT-CACGGAAAACTTGA (SEQ ID NO: 50)

CLC 119 downstream

CCTTCCGGATCCTCATCAAACTGGG-TAAAGTAATTTTT (SEQ ID NO: 51)

CLC 107 and CLC 108 were used in a PCR reaction with a DNA template containing PenI gene. CLC 107 places a HindIII site at the 5' end of the PenI and CLC 108 places a 15 amino acid linker at the 3' end. CLC 109 and CLC 119 were used in a PCR reaction with a DND template containing the GAP-N SH2 gene. CLC 109 places the 15 amino acid linker at the 5' end of the GAP-N SH2 and CLC 119 places a BamHI site at the 3' end. The resulting PCR products from each reaction were then added together in a new PCR reaction with CLC 107 and CLC 119. The resulting fragment containing PenI-linker-SH2 was digested with HinDIII and BamHI and then ligated into the pDG160 expression vector and into the vector pTRP3 downstream from the *E. coli* Trp promoter.

This fusion peptide was expressed in *E. coli* and purified as described in Example 1 above. The results indicate that it is also processed during the purification, similar to the PenI:TnI35 fusion peptide. To maximize recovery of the full length fusion polypeptide from the pDG160 vector 1–10 mm PMSF are added to the cell before breakage. To maximize recovery from the pTRP3 construct the culture is grown at 30° C.

EXAMPLE 6

Comparison of PenI:C9 Muteins vs PenI:C9 wt by Competition ELISA

The HPLC monoS purified PenI:C9 muteins and wild type (wt) (identified in Examples 1 and 3 above and FIG. 3) were tested for their relative binding to the anti-C9 specific protein A purified mAb TA1 in a competitive ELISA. The assay was performed using microtiter plates that had been previously coated with PenI:C9(wt) by a passive technique (10 m ng protein/well). Dilution of the PenI:C9(wt) and the PenI:C9 muteins were preincubated for 1 hour at room temperature with the mAb TA1 that was at a concentration of 271 ng/ml. The plates were washed and 100 μl/well of each sample was applied and incubated at room temperature for ½ hour. The wells were washed and 100 μl/well of a 1:2000 dilution of a Goat anti-mouse IgG HRP conjugate was added. The plated were incubated at room temperature for another ½ hour. The plates were washed again and 100 μl/well of substrate (ABTS) was added and allowed to react for 8 minutes at room temperature. Each well was quenched with 100 μl of 1% SDS stop solution. The ELISA signal was read at 405 nm using a Biotek Plate reader. The data collected was analyzed using EXCEL 4.0 software. The maximum (100%) ELISA signal was determined as the average of values seen for dilution of penI lacking C9 that was allowed to react with TA1 as described above. Inhibition of TA1 binding was compared for all PenI:C9 muteins and PenI:C9 (wt) by using the ELISA signals measured at a concentration of 0.2 μM of the competing PenI:C9 fusion protein. This was the concentration at which PenI:C9 (wt) generated a 50% signal compared to the maximum signal generated in this ELISA. FIG. 5 of the Drawings shows this data expressed as percent binding to TA1 in a bar graph. The results clearly indicate that not all nine amino acid residues are required for binding. The amino terminus of the peptide DSDRAIEGR is shown to be less important to binding to TA1 relative to the carboxy terminus of the peptide. More specifically, the results indicate that the sequence RAIXGR of the peptide contributes to most of the binding of the peptide.

EXAMPLE 7

Cleavage and Purification of the Troponin I 35 Amino Acid Peptide from PenI:TnI Fusion Polypeptide To purify the TnI35 peptide from the fusion protein PenI:TnI35, 23.7 $\mu$g of purified PenI:TnI35 were digested with 0.004 units of Factor Xa (Sigma Diagnostics 870-10) at 37° C. for 30 minutes. The sample was then brought to 0.1% trifluoroacetic acid (TFA) and loaded onto a prepacked Pharmacia PepRPC C2/C18 reverse phase column (0.5×6 cm, 5 $\mu$m particle size), equilibrated with 0.1% TFA in water (solvent A) and connected to a Waters 625 Liquid Chromatography System. The column was eluted with a linear gradient of 0–100% solvent B (0.1% TFA in acetonitrile) in 20 minutes at a flow rate of 1 ml/min. The absorbance of 214 nm was monitored to detect the eluted peptide. The retention time for TnI35 cleaved peptide was 12.2 minutes. This retention time was identical to the identical synthetic peptide run as a control.

EXAMPLE 8

Immunization of Mice with PenI:C9

Part 1. To show the efficacy of the fusion peptide PenI:C9 as a carrier for immunization, Balb/c mice were immunized with F1.2-C9 conjugated to KLH or the F1.2-C9 penI fusion polypeptide of the invention (see Examples 1 and 3 above and FIG. 2) by either intraperitoneal or subcutaneous injection in complete or incomplete Freund's adjuvant respectively as described in the Table shown in FIG. 6 of the Drawings. In that Table the designation "CFA" refers to Complete Freund's Adjuvant, "IFA" refers to Incomplete Freund's Adjuvant, "i.p." refers to intraperitoneally, and "subcut." refers to subcutaneously. Dates of injection are given with reference to the date of sensitization (day 1).

Part 2. The immunized mice were bled and assayed for specific antibody response to the C9 peptide as generally described in the Table shown in FIG. 7 of the Drawings. Specifically, the mice were immunized on day 70 (first boost) and day 101 (second boost) after sensitization with F1.2-C9 KLH #3 and on day 32 after sensitization with the fusion polypeptide F1.2-C9 penI #1 and assayed for specific antibody response to the F1.2-C9 peptide and F2 (truncated F1.2 protein) by a sandwich ELISA assay with antigen (F2 or F1.2-C9 synthetic peptide conjugated to KLH or Ova) coated microtiter plate wells. Controls included sera of mice immunized previously with F1.2-C9 conjugates and TA1 monoclonal (TA1 was raised from a mouse that had been immunized with F1.2-C9 KLH by standard procedures). The titer was determined as the highest dilution producing an ELISA signal equal to or greater than twice that of background.

The results as shown in the Table of FIG. 7 indicated that the mice responded to the PenI:C9 peptide in titers comparable to those of mice immunized with synthetic peptide KLH conjugant.

This invention has been described in detail with reference to preferred embodiments thereof. However, it will be appreciated that those skilled in the art, upon consideration of this disclosure, may make modifications and improvements within the spirit and scope of the invention.

What is claimed is:

1. A method for producing a target peptide, comprising:
(a) providing in solution a fusion polypeptide that comprises a target peptide and a penI protein or precipitation effective portion thereof; and
(b) contacting said polypeptide with an aqueous solution having an ionic strength sufficient to precipitate the fusion polypeptide.

2. The method of claim 1, wherein the polypeptide is contacted with a buffer solution having a salt concentration of about 200 mM salt or less.

3. The method of claim 2, wherein the salt is KCl.

4. The method of claim 1, wherein the fusion polypeptide is in solution in a crude cell extract.

5. The method of claim 1, wherein a linking sequence is interposed between the penI protein or portion thereof and the target peptide.

6. The method of claim 5, wherein the linking sequence comprises a proteolytic cleavage site.

7. The method of claim 6, wherein the cleavage site is a Factor Xa site.

8. The method of claim 1, wherein the target peptide contains about 250 or less amino acids.

9. The method of claim 1, wherein the target peptide contains about 140 or less amino acids.

10. The method of claim 1, wherein the target peptide contains about 70 or less amino acids.

11. The method of claim 1, wherein the polypeptide is contacted with the solution during a dialysis step.

12. The method of claim 11, Wherein the polypeptide is dialyzed against an aqueous solution having a salt concentration of about 100 mM or less.

13. The method of claim 1, wherein the fusion polypeptide is provided by:
(i) synthesizing an expression vector which expresses the fusion polypeptide in a transformed host cell;
(ii) transforming a suitable host cell with the expression vector; and
(iii) culturing the transformed host cell under conditions suitable for the expression of the fusion polypeptide.

14. The method of claim 1, further comprising cleaving the target peptide from the fusion polypeptide.

15. The method of claim 1, wherein the precipitated fusion polypeptide is dissolved in an aqueous solution and then the polypeptide is contacted with a further aqueous solution having an ionic strength sufficient to precipitate the fusion polypeptide.

16. The method of claim 1, wherein said contacting provides the polypeptide in a purity of about 85 percent or greater.

17. A DNA expression vector capable of expressing a penI protein or precipitation effective potion thereof fused to a target peptide, comprising:
   a DNA sequence coding for the penI protein or precipitation effective portion thereof; and
   a DNA sequence coding for the target peptide.

18. The DNA expression vector of claim 17, further comprising a DNA fragment coding for a linking sequence positioned between said DNA sequence coding for penI protein or portion thereof and said DNA sequence coding for the target peptide.

19. The DNA expression vector of claim 18, wherein the DNA fragment coding for a linking sequence comprises one or more cleavage sites.

20. A fusion polypeptide comprising a penI protein or precipitation effective portion thereof fused to a target peptide.

21. The polypeptide of claim 20, wherein a linking segment is interposed between the penI protein or effective portion thereof and the target peptide.

22. The polypeptide of claim 21, wherein the linking segment comprises one or more cleavage sites.

23. A method of immunization of a mammal comprising administering to the mammal a fusion polypeptide that comprises a penI protein or portion thereof fused to a target peptide whereby said administration elicits a desired immune response by the mammal.

24. A method of identifying one or more epitopes of a peptide, comprising:
   producing a fusion polypeptide that comprises a target peptide and a penI protein or precipitation effective portion thereof in accordance with claim 1, and determining the binding activity of the fusion polypeptide, or isolated target peptide portion of the fusion polypeptide, to a binding domain of a selected peptide.

25. The method of claim 24 wherein the selected peptide is an antibody.

26. A method for the selection of a target polypeptide comprising:
   transforming host cells with expression vectors that each contains a gene construct that codes for a fusion polypeptide comprising a target peptide and a penI protein or precipitation effective portion thereof;
   culturing the transformed host cells under conditions suitable for expression of the fusion polypeptide; and
   selecting host cells that express the target polypeptide.

27. The method of claim 26 wherein the target peptide is encoded by a DNA fragment from a genomic DNA library or cDNA library.

28. The method of claim 26 wherein the selected target polypeptide is isolated as a penI fusion polypeptide by contacting the penI fusion polypeptide with a solution having an ionic strength sufficient to precipitate the penI fusion polypeptide.

29. The method of claim 1 wherein the penI protein or precipitation effective portion thereof is derived from *Bacillus licheniformis*.

30. The method of claim 1 wherein the penI protein or precipitation effective portion thereof has at least about 50% amino acid identity to *Bacillus licheniformis* penI protein.

31. The method of claim 1 wherein the penI protein or precipitation effective portion thereof has at least about 70% amino acid identity to *Bacillus licheniformis* penI protein.

32. The method of claim 1 wherein the penI protein or precipitation effective portion thereof has at least about 90% amino acid identity to *Bacillus licheniformis* penI protein.

33. The method of claim 32 wherein the penI protein or precipitation effective portion thereof is derived from *Bacillus licheniformis* and the target peptide has about 200 amino acid residues or less.

34. The method of claim 1 wherein the target peptide has about 200 amino acid residues or less.

35. The expression vector of claim 17 wherein the DNA sequence coding for the penI peptide or precipitation effective portion thereof is derived from *Bacillus licheniformis*.

36. The polypeptide of claim 20 wherein the penI protein or precipitation effective protein thereof is derived from *Bacillus licheniformis*.

37. The method of claim 23 wherein the penI protein or precipitation effective protein thereof is derived from *Bacillus licheniformis*.

38. The method of claim 26 wherein the penI protein or precipitation effective protein thereof is derived from *Bacillus licheniformis*.

* * * * *

SEQUENCE LISTING ( 1 ) GENERAL INFORMATION:

( i i i ) NUMBER OF SEQUENCES: 51

( 2 ) INFORMATION FOR SEQ ID NO:1:

( i ) SEQUENCE CHARACTERISTICS:
( A ) LENGTH: 433 base pairs
( B ) TYPE: nucleic acid
( C ) STRANDEDNESS: unknown
( D ) TOPOLOGY: unknown ( x i ) SEQUENCE DESCRIPTION: SEQ ID NO:1:

```
AAGCTTATGA AAAAAATACC TCAAATCTCT GATGCGGAAT TAGAAGTGAT GAAAGTCATC    60
TGGAAGCATT CTTCGATCAA TACCAATGAG GTAATTAAAG AGTTATCCAA AACCAGTACA   120
TGGAGCCCTA AAACCATCCA AACCATGCTG CTGCGCCTCA TTAAAAAAGG CGCTTTAAAC   180
CACCATAAAG AAGGACGGGT TTTCGTTTAC ACACCAAATA TAGACGAAAG TGATTATATA   240
GAGGTTAAGA GTCACAGTTT TTTAAACCGG TTTTACAATG GAACTCTTAA TTCGATGGTA   300
TTAAACTTTT TGGAGAATGA TCAGCTGTCA GGTGAAGAAA TTAATGAATT GTATCAAATA   360
TTAGAAGAAC ATAAGAACAG AAAGAAGGAA CCATGGGACT CTGACCGTGC AATCGAAGGT   420
CGTTGAGGGA TCC                                                      433
```

( 2 ) INFORMATION FOR SEQ ID NO:2:

( i ) SEQUENCE CHARACTERISTICS:
        ( A ) LENGTH: 37 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:2:

GCATCTGACC GTGCAATCGA AGGTCGTTGA GGGATCC    37

( 2 ) INFORMATION FOR SEQ ID NO:3:

( i ) SEQUENCE CHARACTERISTICS:
        ( A ) LENGTH: 37 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:3:

GACGCTGACC GTGCAATCGAAG GTCGTTGA GGGATCC    37

( 2 ) INFORMATION FOR SEQ ID NO:4:

( i ) SEQUENCE CHARACTERISTICS:
        ( A ) LENGTH: 37 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:4:

GACTCTGCAC GTGCAATCGAAG GTCGTTGA GGGATCC    37

( 2 ) INFORMATION FOR SEQ ID NO:5:

( i ) SEQUENCE CHARACTERISTICS:
        ( A ) LENGTH: 37 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:5:

GACTCTGACG CTGCAATCGA AGGTCGTTGA GGGATCC    37

( 2 ) INFORMATION FOR SEQ ID NO:6:

( i ) SEQUENCE CHARACTERISTICS:
        ( A ) LENGTH: 37 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:6:

GACTCTGACC GTTCCATCGA AGGTCGTTGA GGGATCC    37

( 2 ) INFORMATION FOR SEQ ID NO:7:

( i ) SEQUENCE CHARACTERISTICS:
        ( A ) LENGTH: 37 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:7:

GACTCTGACC GTGCAGCTGA AGGTCGTTGA GGGATCC    37

( 2 ) INFORMATION FOR SEQ ID NO:8:

( i ) SEQUENCE CHARACTERISTICS:
        ( A ) LENGTH: 37 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:8:

GACTCTGACC GTGCAATCGC TGGTCGTTGA GGGATCC　　　　　37

( 2 ) INFORMATION FOR SEQ ID NO:9:

( i ) SEQUENCE CHARACTERISTICS:
        ( A ) LENGTH: 37 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:9:

GACTCTGACC GTGCAATCGA AGCACGTTGA GGGATCC　　　　　37

( 2 ) INFORMATION FOR SEQ ID NO:10:

( i ) SEQUENCE CHARACTERISTICS:
        ( A ) LENGTH: 37 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:10:

GACTCTGACC GTGCAATCGA AGGCGCATGA GGGATCC　　　　　37

( 2 ) INFORMATION FOR SEQ ID NO:11:

( i ) SEQUENCE CHARACTERISTICS:
        ( A ) LENGTH: 141 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:11:

```
Lys Leu Met Lys Lys Ile Pro Gln Ile Ser Asp Ala Glu Leu Glu Val
 1               5                  10                  15
Met Lys Val Ile Trp Lys His Ser Ser Ile Asn Thr Asn Glu Val Ile
            20                  25                  30
Lys Glu Leu Ser Lys Thr Ser Thr Trp Ser Pro Lys Thr Ile Gln Thr
            35                  40                  45
Met Leu Leu Arg Leu Ile Lys Lys Gly Ala Leu Asn His His Lys Glu
    50                  55                  60
Gly Arg Val Phe Val Tyr Thr Pro Asn Ile Asp Glu Ser Asp Tyr Ile
65                  70                  75                  80
Glu Val Lys Ser His Ser Phe Leu Asn Arg Phe Tyr Asn Gly Thr Leu
                85                  90                  95
Asn Ser Met Val Leu Asn Phe Leu Glu Asn Asp Gln Leu Ser Gly Glu
                100                 105                 110
Glu Ile Asn Glu Leu Tyr Gln Ile Leu Glu Glu His Lys Asn Arg Lys
            115                 120                 125
Lys Glu Pro Trp Asp Ser Asp Arg Ala Ile Glu Gly Arg
        130                 135                 140
```

( 2 ) INFORMATION FOR SEQ ID NO:12:

( i ) SEQUENCE CHARACTERISTICS:

(A) LENGTH: 9 amino acids
(B) TYPE: amino acid
(C) STRANDEDNESS: unknown
(D) TOPOLOGY: unknown (xi) SEQUENCE DESCRIPTION: SEQ ID NO:12:

Ala Ser Asp Arg Ala Ile Glu Gly Arg
1               5

(2) INFORMATION FOR SEQ ID NO:13:

(i) SEQUENCE CHARACTERISTICS:
(A) LENGTH: 9 amino acids
(B) TYPE: amino acid
(C) STRANDEDNESS: unknown
(D) TOPOLOGY: unknown (xi) SEQUENCE DESCRIPTION: SEQ ID NO:13:

Asp Ala Asp Arg Ala Ile Glu Gly Arg
1               5

(2) INFORMATION FOR SEQ ID NO:14:

(i) SEQUENCE CHARACTERISTICS:
(A) LENGTH: 9 amino acids
(B) TYPE: amino acid
(C) STRANDEDNESS: unknown
(D) TOPOLOGY: unknown (xi) SEQUENCE DESCRIPTION: SEQ ID NO:14:

Asp Ser Ala Arg Ala Ile Glu Gly Arg
1               5

(2) INFORMATION FOR SEQ ID NO:15:

(i) SEQUENCE CHARACTERISTICS:
(A) LENGTH: 9 amino acids
(B) TYPE: amino acid
(C) STRANDEDNESS: unknown
(D) TOPOLOGY: unknown (xi) SEQUENCE DESCRIPTION: SEQ ID NO:15:

Asp Ser Asp Ala Ala Ile Glu Gly Arg
1               5

(2) INFORMATION FOR SEQ ID NO:16:

(i) SEQUENCE CHARACTERISTICS:
(A) LENGTH: 9 amino acids
(B) TYPE: amino acid
(C) STRANDEDNESS: unknown
(D) TOPOLOGY: unknown (xi) SEQUENCE DESCRIPTION: SEQ ID NO:16:

Asp Ser Asp Arg Ser Ile Glu Gly Arg
1               5

(2) INFORMATION FOR SEQ ID NO:17:

(i) SEQUENCE CHARACTERISTICS:
(A) LENGTH: 9 amino acids
(B) TYPE: amino acid
(C) STRANDEDNESS: unknown
(D) TOPOLOGY: unknown (xi) SEQUENCE DESCRIPTION: SEQ ID NO:17:

Asp Ser Asp Arg Ala Ala Glu Gly Arg
1               5

( 2 ) INFORMATION FOR SEQ ID NO:18:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:18:

```
Asp  Ser  Asp  Arg  Ala  Ile  Ala  Gly  Arg
1                   5
```

( 2 ) INFORMATION FOR SEQ ID NO:19:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:19:

```
Asp  Ser  Asp  Arg  Ala  Ile  Glu  Ala  Arg
1                   5
```

( 2 ) INFORMATION FOR SEQ ID NO:20:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:20:

```
Asp  Ser  Asp  Arg  Ala  Ile  Glu  Gly  Ala
1                   5
```

( 2 ) INFORMATION FOR SEQ ID NO:21:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:21:

GGAAGCTTAT GAAAAAAATA CCTC    24

( 2 ) INFORMATION FOR SEQ ID NO:22:

( i ) SEQUENCE CHARACTERISTICS:
        ( A ) LENGTH: 34 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:22:

GGGGATCCCT CACCATGGTT CCTTCTTTCT GTTC    34

( 2 ) INFORMATION FOR SEQ ID NO:23:

( i ) SEQUENCE CHARACTERISTICS:
        ( A ) LENGTH: 11 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:23:

ATCGAGGTAG G    11

( 2 ) INFORMATION FOR SEQ ID NO:24:

( i ) SEQUENCE CHARACTERISTICS:
    ( A ) LENGTH: 24 base pairs
    ( B ) TYPE: nucleic acid
    ( C ) STRANDEDNESS: unknown
    ( D ) TOPOLOGY: unknown ( x i ) SEQUENCE DESCRIPTION: SEQ ID NO:24:

GGAAGCTTAT GAAAAAATA CCTC                     24

( 2 ) INFORMATION FOR SEQ ID NO:25:

( i ) SEQUENCE CHARACTERISTICS:
    ( A ) LENGTH: 34 base pairs
    ( B ) TYPE: nucleic acid
    ( C ) STRANDEDNESS: unknown
    ( D ) TOPOLOGY: unknown ( x i ) SEQUENCE DESCRIPTION: SEQ ID NO:25:

GGGGATCCCT CACCATGGTT CCTTCTTTCT GTTC            34

( 2 ) INFORMATION FOR SEQ ID NO:26:

( i ) SEQUENCE CHARACTERISTICS:
    ( A ) LENGTH: 47 base pairs
    ( B ) TYPE: nucleic acid
    ( C ) STRANDEDNESS: unknown
    ( D ) TOPOLOGY: unknown ( x i ) SEQUENCE DESCRIPTION: SEQ ID NO:26:

CATGGGACTC TGACCGTGCA ATCGAAGGTC GTTGAGGGAT CCGGTAC     47

( 2 ) INFORMATION FOR SEQ ID NO:27:

( i ) SEQUENCE CHARACTERISTICS:
    ( A ) LENGTH: 39 base pairs
    ( B ) TYPE: nucleic acid
    ( C ) STRANDEDNESS: unknown
    ( D ) TOPOLOGY: unknown ( x i ) SEQUENCE DESCRIPTION: SEQ ID NO:27:

CGGATCCCTC AACGACCTTC GATTGCACGG TCAGAGTCC         39

( 2 ) INFORMATION FOR SEQ ID NO:28:

( i ) SEQUENCE CHARACTERISTICS:
    ( A ) LENGTH: 37 base pairs
    ( B ) TYPE: nucleic acid
    ( C ) STRANDEDNESS: unknown
    ( D ) TOPOLOGY: unknown ( x i ) SEQUENCE DESCRIPTION: SEQ ID NO:28:

CATGGGCATC TGACCGTGCA ATCGAAGGTC GTTGAGG          37

( 2 ) INFORMATION FOR SEQ ID NO:29:

( i ) SEQUENCE CHARACTERISTICS:
    ( A ) LENGTH: 37 base pairs
    ( B ) TYPE: nucleic acid
    ( C ) STRANDEDNESS: unknown
    ( D ) TOPOLOGY: unknown ( x i ) SEQUENCE DESCRIPTION: SEQ ID NO:29:

GATCCCTCAA CGACCTTCGA TTGCACGGTC AGATGCC          37

(2) INFORMATION FOR SEQ ID NO:30:

(i) SEQUENCE CHARACTERISTICS:
        (A) LENGTH: 37 base pairs
        (B) TYPE: nucleic acid
        (C) STRANDEDNESS: unknown
        (D) TOPOLOGY: unknown (xi) SEQUENCE DESCRIPTION: SEQ ID NO:30:

```
CATGGGACGC TGACCGTGCA ATCGAAGGTC GTTGAGG                                    37
```

(2) INFORMATION FOR SEQ ID NO:31:

(i) SEQUENCE CHARACTERISTICS:
        (A) LENGTH: 37 base pairs
        (B) TYPE: nucleic acid
        (C) STRANDEDNESS: unknown
        (D) TOPOLOGY: unknown (xi) SEQUENCE DESCRIPTION: SEQ ID NO:31:

```
GATCCCTCAA CGACCTTCGA TTGCACGGTC AGCGTCC                                    37
```

(2) INFORMATION FOR SEQ ID NO:32:

(i) SEQUENCE CHARACTERISTICS:
        (A) LENGTH: 37 base pairs
        (B) TYPE: nucleic acid
        (C) STRANDEDNESS: unknown
        (D) TOPOLOGY: unknown (xi) SEQUENCE DESCRIPTION: SEQ ID NO:32:

```
CATGGGACTC TGCACGTGCA ATCGAAGGTC GTTGAGG                                    37
```

(2) INFORMATION FOR SEQ ID NO:33:

(i) SEQUENCE CHARACTERISTICS:
        (A) LENGTH: 37 base pairs
        (B) TYPE: nucleic acid
        (C) STRANDEDNESS: unknown
        (D) TOPOLOGY: unknown (xi) SEQUENCE DESCRIPTION: SEQ ID NO:33:

```
GATCCCTCAA CGACCTTCGA TTGCACGTGC AGAGTCC                                    37
```

(2) INFORMATION FOR SEQ ID NO:34:

(i) SEQUENCE CHARACTERISTICS:
        (A) LENGTH: 37 base pairs
        (B) TYPE: nucleic acid
        (C) STRANDEDNESS: unknown
        (D) TOPOLOGY: unknown (xi) SEQUENCE DESCRIPTION: SEQ ID NO:34:

```
CATGGGACTC TGACGCTGCA ATCGAAGGTC GTTGAGG                                    37
```

(2) INFORMATION FOR SEQ ID NO:35:

(i) SEQUENCE CHARACTERISTICS:
        (A) LENGTH: 37 base pairs
        (B) TYPE: nucleic acid
        (C) STRANDEDNESS: unknown
        (D) TOPOLOGY: unknown (xi) SEQUENCE DESCRIPTION: SEQ ID NO:35:

```
GATCCCTCAA CGACCTTCGA TTGCAGCGTC AGAGTCC                                    37
```

(2) INFORMATION FOR SEQ ID NO:36:

( i ) SEQUENCE CHARACTERISTICS:
 ( A ) LENGTH: 37 base pairs
 ( B ) TYPE: nucleic acid
 ( C ) STRANDEDNESS: unknown
 ( D ) TOPOLOGY: unknown ( x i ) SEQUENCE DESCRIPTION: SEQ ID NO:36:

CATGGACTC TGACCGTTCC ATCGAAGGTC GTTGAGG 37

( 2 ) INFORMATION FOR SEQ ID NO:37:

( i ) SEQUENCE CHARACTERISTICS:
      ( A ) LENGTH: 37 base pairs
      ( B ) TYPE: nucleic acid
      ( C ) STRANDEDNESS: unknown
      ( D ) TOPOLOGY: unknown ( x i ) SEQUENCE DESCRIPTION: SEQ ID NO:37:

GATCCCTCAA CGACCTTCGA TGGAACGGTC AGAGTCC 37

( 2 ) INFORMATION FOR SEQ ID NO:38:

( i ) SEQUENCE CHARACTERISTICS:
      ( A ) LENGTH: 37 base pairs
      ( B ) TYPE: nucleic acid
      ( C ) STRANDEDNESS: unknown
      ( D ) TOPOLOGY: unknown ( x i ) SEQUENCE DESCRIPTION: SEQ ID NO:38:

CATGGGACTC TGACCGTGCA GCTGAAGGTC GTTGAGG 37

( 2 ) INFORMATION FOR SEQ ID NO:39:

( i ) SEQUENCE CHARACTERISTICS:
      ( A ) LENGTH: 37 base pairs
      ( B ) TYPE: nucleic acid
      ( C ) STRANDEDNESS: unknown
      ( D ) TOPOLOGY: unknown ( x i ) SEQUENCE DESCRIPTION: SEQ ID NO:39:

GATCCCTCAA CGACCTTCAG CTGCACGGTC AGAGTCC 37

( 2 ) INFORMATION FOR SEQ ID NO:40:

( i ) SEQUENCE CHARACTERISTICS:
      ( A ) LENGTH: 37 base pairs
      ( B ) TYPE: nucleic acid
      ( C ) STRANDEDNESS: unknown
      ( D ) TOPOLOGY: unknown ( x i ) SEQUENCE DESCRIPTION: SEQ ID NO:40:

CATGGGACTC TGACCGTGCA ATCGCTGGTC GTTGAGG 37

( 2 ) INFORMATION FOR SEQ ID NO:41:

( i ) SEQUENCE CHARACTERISTICS:
      ( A ) LENGTH: 37 base pairs
      ( B ) TYPE: nucleic acid
      ( C ) STRANDEDNESS: unknown
      ( D ) TOPOLOGY: unknown ( x i ) SEQUENCE DESCRIPTION: SEQ ID NO:41:

GATCCCTCAA CGACCAGCGA TTGCACGGTC AGAGTCC 37

( 2 ) INFORMATION FOR SEQ ID NO:42:

( i ) SEQUENCE CHARACTERISTICS:
      ( A ) LENGTH: 37 base pairs ( B ) TYPE: nucleic acid
( C ) STRANDEDNESS: unknown
( D ) TOPOLOGY: unknown ( x i ) SEQUENCE DESCRIPTION: SEQ ID NO:42:

CATGGGACTC TGACCGTGCA ATCGAAGCAC GTTGAGG    37

( 2 ) INFORMATION FOR SEQ ID NO:43:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:43:

GATCCCTCAA CGTGCTTCGAT TGCACGGTCA GAGTCC    37

( 2 ) INFORMATION FOR SEQ ID NO:44:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:44:

CATGGGACTC TGACCGTGCA ATCGAAGGCG CATGAGG    37

( 2 ) INFORMATION FOR SEQ ID NO:45:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:45:

GATCCCTCAT GCGCCTTCGA TTGCACGGTC AGAGTCC    37

( 2 ) INFORMATION FOR SEQ ID NO:46:

( i ) SEQUENCE CHARACTERISTICS:
( A ) LENGTH: 43 base pairs
( B ) TYPE: nucleic acid
( C ) STRANDEDNESS: unknown
( D ) TOPOLOGY: unknown ( x i ) SEQUENCE DESCRIPTION: SEQ ID NO:46:

GGGGCCATGG ATCGAAGGTC GTACTAGTCG CGCTTATGCC ACG    43

( 2 ) INFORMATION FOR SEQ ID NO:47:

( i ) SEQUENCE CHARACTERISTICS:
( A ) LENGTH: 34 base pairs
( B ) TYPE: nucleic acid
( C ) STRANDEDNESS: unknown
( D ) TOPOLOGY: unknown ( x i ) SEQUENCE DESCRIPTION: SEQ ID NO:47:

CCCCGGATCC TCACAGCTCT TGCTTTGCAA TCGT    34

( 2 ) INFORMATION FOR SEQ ID NO:48:

( i ) SEQUENCE CHARACTERISTICS:
( A ) LENGTH: 32 base pairs
( B ) TYPE: nucleic acid
( C ) STRANDEDNESS: unknown (D) TOPOLOGY: unknown (xi) SEQUENCE DESCRIPTION: SEQ ID NO:48:

GAGAGAAAGC TTATGAAAAA AATACCTCAA AT 32

(2) INFORMATION FOR SEQ ID NO:49:

(i) SEQUENCE CHARACTERISTICS:
    (A) LENGTH: 65 base pairs
    (B) TYPE: nucleic acid
    (C) STRANDEDNESS: unknown
    (D) TOPOLOGY: unknown (xi) SEQUENCE DESCRIPTION: SEQ ID NO:49:

GGAGCCGCCA CCACCGCTGC CACCACCGCC AGAACGCCG CCACCTTCCT TCTTTCTGTT 60

CTTAT 65

(2) INFORMATION FOR SEQ ID NO:50:

(i) SEQUENCE CHARACTERISTICS:
    (A) LENGTH: 68 base pairs
    (B) TYPE: nucleic acid
    (C) STRANDEDNESS: unknown
    (D) TOPOLOGY: unknown (xi) SEQUENCE DESCRIPTION: SEQ ID NO:50:

GGTGGCGGCG GTTCTGGCGG TGGTGGCAGC GGTGGTGGCG GCTCCTGGTG GTATCACGGA 60

AAACTTGA 68

(2) INFORMATION FOR SEQ ID NO:51:

(i) SEQUENCE CHARACTERISTICS:
    (A) LENGTH: 38 base pairs
    (B) TYPE: nucleic acid
    (C) STRANDEDNESS: unknown
    (D) TOPOLOGY: unknown (xi) SEQUENCE DESCRIPTION: SEQ ID NO:51:

CCTTCCGGAT CCTCATCAAA CTGGGTAAAG TAATTTTT 38